United States Patent [19]

Merger et al.

[11] Patent Number: 4,665,219

[45] Date of Patent: May 12, 1987

[54] ISOLATION OF NEOPENTYL GLYCOL HYDROXYPIVALATE

[75] Inventors: Franz Merger, Frankenthal; Peter Hettinger, Edingen-Neckarhausen; Theodor Weber, Ludwigshafen; Guenter Boettger, Bad Durkheim; Wolfgang Koernig, Dossenheim, all of Fed. Rep. of Germany

[73] Assignee: BASF Aktiengesellschaft, Ludwigshafen, Fed. Rep. of Germany

[21] Appl. No.: 772,841

[22] Filed: Sep. 5, 1985

[30] Foreign Application Priority Data

Sep. 5, 1984 [DE] Fed. Rep. of Germany ....... 3432577

[51] Int. Cl.$^4$ .................... C07C 69/66; B01D 3/00
[52] U.S. Cl. ..................... 560/189; 203/38; 203/39; 203/89
[58] Field of Search ............. 560/189; 203/43–46, 203/39, 92, 95, 96, 97, 93, 89; 159/47.1, 49

[56] References Cited

U.S. PATENT DOCUMENTS

| | | | |
|---|---|---|---|
| 3,641,117 | 2/1972 | Platz et al. | 560/189 |
| 3,641,118 | 2/1972 | Platz et al. | 560/189 |
| 3,696,005 | 10/1972 | Fuchs et al. | 560/189 |
| 3,852,335 | 12/1974 | Merger et al. | 560/189 |
| 3,862,215 | 1/1975 | Merger et al. | 560/189 |

FOREIGN PATENT DOCUMENTS 1524612 9/1978 United Kingdom.

*Primary Examiner*—Wilbur Bascomb
*Attorney, Agent, or Firm*—John H. Shurtleff

[57] ABSTRACT

Neopentyl glycol hydroxypivalate is isolated from a reaction mixture obtained from a Tishchenko reaction of hydroxypivalaldehyde in the presence of calcium hydroxide, barium hydroxide or strontium hydroxide, by adding acid, removing the salts formed by adjusting the water content in the reaction mixture to 20–60% and extracting the salts at above 50° C. and working up the residual mixture by distillation.

13 Claims, No Drawings

ISOLATION OF NEOPENTYL GLYCOL HYDROXYPIVALATE

The present invention relates to an improved process for isolating neopentyl glycol hydroxypivalate (I) from a reaction mixture which is obtained by reacting hydroxypivalaldehyde (II) in the presence of calcium hydroxide, barium hydroxide or strontium hydroxide as the catalyst and subsequent acid treatment, by removing the salts formed and working up the residual mixture by distillation to give (I).

The preparation of (I) by a Tishchenko reaction (disproportionation) in the presence of a catalytic amount of calcium hydroxide, barium hydroxide or strontium hydroxide, in accordance with the equation

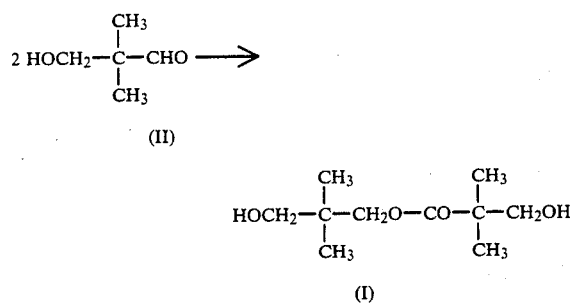

is well known. Moreover it is known, for example from German Laid-Open Application DOS No. 2,234,358 that the reaction mixture thus obtained may advantageously be acidified before being worked up to give (I), the acidification giving the corresponding salt. However, the isolation of (I) from the salt-containing reaction mixture presents difficulties since the salt is present partially in a dissolved and partially in an undissolved form. To the extent that they are solid, the salts have to be filtered off, and such filtration always presents technical problems, and to the extent that it is dissolved the salt precipitates during distillation and forms crusts in the distillation apparatus, which in turn—especially when operating on an industrial scale—result in poor heat transfer and decomposition of the desired product.

The process of German Laid-Open Application DOS No. 2,234,358 solves the problem of salt separating out by converting the base to the formate by means of formic acid; the formate could then be filtered off since it is substantially insoluble in the reaction mixture.

Since, however, this did not eliminate the disadvantages associated with filtration, it is the object of the present invention to provide a technically simpler and hence more economical method of isolating (I) from a Tishchenko reaction mixture.

We have found that this object is achieved by an improved process for isolating neopentyl glycol hydroxypivalate (2,2-dimethyl-propane-1,3-diol monohydroxypivalate) from a reaction mixture which is obtained by reaction of hydroxypivalaldehyde in the presence of calcium hydroxide, barium hydroxide or strontium hydroxide as the catalyst and subsequent acid treatment, by removing the salts thereby formed and working up the residual mixture by distillation to give neopentyl glycol hydroxypivalate, wherein, to remove the salts, the water content in the reaction mixture is adjusted to from 20% to 60% and the salt is extracted at from 50° to 100° C.

The fact that this process succeeds well is noteworthy because, given the solubility of the reactants in water (the solubility of the desired product (I) in water increases with temperature) it was not to be expected that satisfactory separation into a salt-containing aqueous phase and a substantially salt-free organic phase would take place.

Suitable acids for the acid treatment are those which are readily water-soluble and preferably those which are stronger acids than hydroxypivalic acid, ie., for example, hydrochloric acid, acetic acid, citric acid and especially formic acid.

To the Tishchenko reaction mixture, which is weakly basic, are added 0.4–3.0 moles, especially 0.5 to 2.0 moles, of acid, per mole of catalyst, to complete the neutralization before the aqueous extraction; this causes the mixture to be weakly acid or, preferably, neutral. The acid may be used undiluted or as its aqueous solution and is added at not below 50° C. and advantageously at from 60° to 80° C.

For extraction, as much water as is needed to dissolve the salt is added to the reaction mixture at from 50° to 100° C., advantageously from 60° to 80° C., especially from 65° to 75° C. As a rule this corresponds to bringing the water content to 20–60%, advantageously 20–40%.

The measure provided by the invention, of carrying out the extraction at an elevated temperature, is based not solely on an increase in salt solubility with temperature but in particular also on the fact that only at above 50° C. can phase separation into a saline aqueous phase and a substantially salt-free organic phase be achieved within a reasonable time, as a rule within from 10 to 30 minutes.

When using acetic acid to neutralize the reaction mixture it would, for example, suggest itself that the extraction should be carried out at low a temperature as possible, since the acetates show an inverse solution characteristic; in that case, however, only a milky emulsion is obtained, even after several hours. Only on increasing the temperature does phase separation occur.

The extraction is carried out by the conventional techniques, continuously or batchwise, so that no further details need be given here.

Using the process according to the invention, the degree of desalination of the organic phase is from 80 to 90%, based on the amount of hydroxide employed. Further depletion, to 5% of the salts being present in the crude end product, can be achieved by repeating the extraction under the same conditions. To avoid losses in yield of (I), the aqueous phase obtained in the second extraction is advantageously introduced into the first extraction stage of a further batch.

The crude product obtained after extraction can be isolated by fractional distillation using the conventional techniques. Because of the low salt content of the crude product, a thin film evaporator can also be used advantageously, in which case the desired product (I) is obtained in high purity and a high yield can be isolated.

The compound (I) is known as a valuable starting material for the preparation of polyesters, synthetic resins and plasticizers.

EXAMPLE 1

101 parts of 37% strength aqueous formaldehyde solution and 99 parts of isobutyraldehyde were mixed with 4.2 parts of 40% strength aqueous trimethylamine solution by stirring at 40° C. under nitrogen. The temperature of the mixture, kept under a reflux condenser, rose in 15–20 minutes to 93°–94° C. It was then stirred for a further 10 minutes at the same temperature, and thereafter the trimethylamine, the excess isobutyraldehyde and 58 parts of water were distilled off under reduced pressure. The hydroxypivalaldehyde solution which remained was then cooled to 60° C. and 1.9 parts of finely powdered calcium hydroxide were added, with vigorous stirring.

The reaction mixture rose to the boil within 15–20 minutes; the excess heat was removed by evaporative cooling. When the heat evolution had subsided and the mixture had briefly been stirred further (for a total of 45 minutes), 2.5 of 100% strength formic acid were added at 70° C. and stirring continued for 10 minutes.

62 parts of water were then added and the mixture was stirred at 70° C. for 10 minutes. Phase separation took place within 15 minutes. The lower aqueous phase was then drained off and the organic phase subjected to fractional distillation. 110 parts of 2,2-dimethyl-propane-1,3-diol monohydroxypivalate, of boiling point 120°–122°0 C. at 1.33 mbar, were isolated, corresponding to 85.9% of theory based on formaldehyde employed. The distillation residue was 0.7 part of inorganic salts, corresponding to 0.37% based on the organic phase separated off.

EXAMPLE 2

A crude reaction mixture of 2,2-dimethyl-propane-1,3-diol monohydroxypivalate, prepared similarly to Example 1, was treated with 0.6 part of 100% strength formic acid at 75° C. and stirred for 10 minutes. 63 parts of water were then added to the mixture, the batch was stirred for 10 minutes at 75° C., phase separation was allowed to occur and after 20 minutes the lower aqueous phase was separated off. Analysis of the organic phase showed a salt content of 0.1% (calculated as calcium formate). Renewed treatment of the organic phase with 63 parts of water under the above conditions reduced the salt content of the organic phase to 0.02% (calculated as calcium formate). The organic phase (157 parts) contained, according to gas chromatography, 60.2% by weight of 2,2-dimethyl-propane-1,3-diol monohydroxypivalate (corresponding to 75% of theory, based on formaldehyde employed). The aqueous phase from the second extraction, which could be recycled to the next batch, contained, according to gas chromatography, 13.3% by weight (58 parts) of 2,2-dimethyl-propane-1,3-diol monohydroxypivalate, corresponding to 6.1% of theory, based on formaldehyde employed.

EXAMPLE 3

A crude reaction mixture originating from the calcium hydroxide-catalyzed Tishchenko reaction of 375 g of hydroxypivalaldehyde and additionally containing 12 g of water, was treated with 10.2 g of glacial acetic acid at 70° C. and stirred for 10 minutes. 120 g of water were then added, the mixture was stirred at 70° C. for 15 minutes and when phase separation had taken place the lower aqueous phase was separated off. Analytical determination of the salt content of the organic phase gave a value of 1.42% (calculated as calcium acetate).

Fractional distillation of the organic phase resulted, after first runnings of 65 g of uncoverted hydroxypivalaldehyde, in the isolation of 275 g of 2,2-dimethyl-propane-1,3-diol monohydroxypivalate of boiling point 119°–121° C. at 1.33 mbar, corresponding to 80% of theory based on hydroxypivalaldehyde converted.

EXAMPLE 4

A crude reaction mixture of 2,2-dimethyl-propane-1,3-diol monohydroxypivalate, prepared similarly to Example 1, was mixed with 2.5 parts of formic acid and 63 parts of water at 75° C. and the batch was stirred for 15 minutes. When phase separation had occurred, the lower phase was separated off and the organic phase was again treated with 63 parts of water, for 15 minutes at 75° C., after which the salt content of the organic phase was 0.07% (calculated as calcium formate).

After phase separation at 75° C. and removal of low-boiling components by distillation under reduced pressure, the crude 2,2-dimethyl-propane-1,3-diol monohydroxypivalate was isolated by distillation at 1.33 mbar using a SAMBAY evaporator.

The bottom fraction resulting at the same time amounted to 1.1%, based on the distillate, and caused no technical problems during distillation.

We claim:

1. In a process for the recovery of neopentyl glycol hydroxypivalate

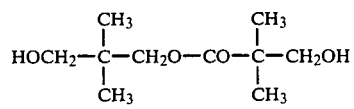

from a reaction mixture obtained by the Tishchenko reaction of hydroxypivalaldehyde

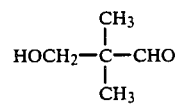

in the presence of calcium, strontium or barium hydroxide as the catalyst, subsequent neutralization of the mixture with an acid, removal of the salts thus formed, and isolation of said compound I, the improvement comprising:

carrying out the removal of the salts by a liquid-liquid extraction which includes the steps of
adding sufficient water to dissolve the salt formed by neutralization and to bring the water content of said reaction mixture to 20 to 60% by weight,
stirring the mixture at from 50° to 100° C.,
allowing the stirred mixture to stand at from 50° to 100° C. for a period of time sufficient to form an aqueous phase which contains at least a predominant amount of the salt formed by said neutralization and an organic phase containing the compound I and any residual salt not dissolved in the aqueous phase, and
thereafter separating the aqueous phase containing the dissolved salt from the organic phase containing the compound I.

2. A process as claimed in claim 1, wherein the acid used for neutralization is formic acid.

3. A process as claimed in claim 2, wherein from 0.4 to 3.0 moles of formic acid are used per mole of original catalyst.

4. A process as claimed in claim 1, wherein the pH of the reaction mixture is brought to 3–7 in the neutralization step before extraction.

5. A process as claimed in claim 1, wherein the extraction is carried out at from 60° to 80° C.

6. A process as claimed in claim 1, wherein the water content of the reaction mixture is brought to between 20 and 40% when adding water to dissolve the salt.

7. A process as claimed in claim 1, wherein the separated aqueous phase contains a predominant amount of the salt formed by the neutralization and the organic phase contains the remainder of said salt formed by the neutralization.

8. A process as claimed in claim 1, wherein the extraction is carried out at a temperature of from 65° to 75° C.

9. A process as claimed in claim 1, wherein the compound I is recovered by fractional distillation of the separated organic phase.

10. A process as claimed in claim 1, wherein the compound I is recovered by evaporation of the separated organic phase.

11. A process as claimed in claim 8, wherein the degree of desalination of the organic phase after extraction is at least about 80%.

12. A process as claimed in claim 11, wherein said degree of desalination is about 95% after repeating the extraction under the same conditions.

13. A process as claimed in claim 12, wherein the aqueous phase obtained after the repeated extraction is recycled to a first extraction step.

* * * * *

UNITED STATES PATENT AND TRADEMARK OFFICE
CERTIFICATE OF CORRECTION

PATENT NO. : 4,665,219

DATED : May 12, 1987

INVENTOR(S) : Franz Merger, Peter Hettinger, Theodor Weber, Guenter Boettger and Wolfgang Koernig It is certified that error appears in the above-identified patent and that said Letters Patent is hereby corrected as shown below:

Claim 11, line 1: change the numeral "8" to --1--.

Signed and Sealed this

Twenty-ninth Day of September, 1987

*Attest:*

DONALD J. QUIGG

*Attesting Officer*  *Commissioner of Patents and Trademarks*